(12) United States Patent
Teichtmann

(10) Patent No.: US 10,413,375 B2
(45) Date of Patent: Sep. 17, 2019

(54) INSTRUMENT, IN PARTICULAR A MEDICAL ENDOSCOPIC INSTRUMENT OR TECHNOSCOPE

(71) Applicant: RICHARD WOLF GMBH, Knittlingen (DE)

(72) Inventor: Elmar Teichtmann, Bretten (DE)

(73) Assignee: RICHARD WOLF GMBH, Knittlingen (DE)

( * ) Notice: Subject to any disclaimer, the term of this patent is extended or adjusted under 35 U.S.C. 154(b) by 98 days.

(21) Appl. No.: 15/101,225

(22) PCT Filed: Nov. 10, 2014

(86) PCT No.: PCT/DE2014/200624
§ 371 (c)(1),
(2) Date: Jun. 2, 2016

(87) PCT Pub. No.: WO2015/081946
PCT Pub. Date: Jun. 11, 2015

(65) Prior Publication Data
US 2016/0302876 A1  Oct. 20, 2016

(30) Foreign Application Priority Data
Dec. 3, 2013  (DE) .................. 10 2013 224 753

(51) Int. Cl.
*A61B 34/00* (2016.01)
*A61B 34/30* (2016.01)
(Continued)

(52) U.S. Cl.
CPC .............. *A61B 34/71* (2016.02); *A61B 34/30* (2016.02); *A61B 17/29* (2013.01);
(Continued)

(58) Field of Classification Search
CPC ......... A61B 34/71; A61B 34/30; A61B 17/29; A61B 2034/305; A61B 2017/2927; A61B 2017/00323
See application file for complete search history.

(56) References Cited

U.S. PATENT DOCUMENTS

| | | |
|---|---|---|
| 5,710,870 A | 1/1998 | Ohm et al. |
| 2004/0199147 A1 | 10/2004 | Nishizawa et al. |

(Continued)

FOREIGN PATENT DOCUMENTS

| | | |
|---|---|---|
| EP | 1 886 630 A2 | 2/2008 |
| EP | 2 014 252 A2 | 1/2009 |

(Continued)

*Primary Examiner* — Rex R Holmes
(74) *Attorney, Agent, or Firm* — McGlew and Tuttle, P.C.

(57) ABSTRACT

An instrument, particularly a medical endoscopic instrument or technoscope, includes a shank (2) and an instrument head (6). The instrument head includes at least one joint part (12) articulated on the distal shank end in an angularly bendable manner and a tool carrier (14) which at the distal side is articulated on the joint part (12) in an angularly bendable manner in the angular bending plane of the joint part (12). A toothing is meshed with a toothed body (26) rotatably mounted in the shank (2) and is coupled in movement to a pull cable pair for the movement control of the instrument head (6). The toothing is formed at the proximal end of the joint part (12).

20 Claims, 3 Drawing Sheets

(51) Int. Cl.
*A61B 17/00* (2006.01)
*A61B 17/29* (2006.01)

(52) U.S. Cl.
CPC ............ *A61B 2017/00323* (2013.01); *A61B 2017/2927* (2013.01); *A61B 2034/305* (2016.02)

(56) References Cited

U.S. PATENT DOCUMENTS

| | | | |
|---|---|---|---|
| 2007/0023477 A1 | 2/2007 | Whitman et al. | |
| 2007/0208375 A1* | 9/2007 | Nishizawa | A61B 17/29 606/205 |
| 2009/0031842 A1* | 2/2009 | Kawai | A61B 17/29 74/490.01 |
| 2009/0095790 A1* | 4/2009 | Whitman | A61B 17/07207 227/175.1 |

FOREIGN PATENT DOCUMENTS

| | | |
|---|---|---|
| JP | H06-42609 A | 2/1994 |
| JP | 2004-122286 A | 4/2004 |
| JP | 2013-514861 A | 5/2013 |
| WO | 2009/079781 A1 | 7/2009 |
| WO | 2011078971 A1 | 6/2011 |
| WO | 2013/140426 A1 | 9/2013 |

\* cited by examiner

INSTRUMENT, IN PARTICULAR A MEDICAL ENDOSCOPIC INSTRUMENT OR TECHNOSCOPE

CROSS REFERENCE TO RELATED APPLICATIONS

This application is a United States National Phase Application of International Application PCT/DE2014/200624 filed Nov. 10, 2014 and claims the benefit of priority under 35 U.S.C. § 119 of German Application 10 2013 224 753.2 filed Dec. 3, 2013 the entire contents of which are incorporated herein by reference.

FIELD OF THE INVENTION

The invention relates to an instrument and in particular to a medical-endoscopic instrument or to a technoscope.

BACKGROUND OF THE INVENTION

Shank instruments which at the distal end of a shank comprise an instrument head with a tool arranged on this head are applied in the field of medicine and there in particular in the field of endoscopy. Instruments of this type, with which it can be the case of gripping or cutting instruments, are moreover applied in other fields, for example with technoscopes for the application in cavities of technical objects.

The starting point of the invention is formed by those instruments, with which the instrument head can be angled (bent) relative to the shank, and the tool or at least a part of the tool can be angled relative to a tool carrier of the instrument head. Such an instrument is known from US 2007/0208375 A1. This instrument comprises an instrument head which is arranged distally of a shank and which comprises a tool carrier articulated on the distal end of the shank via an elongate joint part. The tool carrier is articulated on the distal end of the joint part in an angularly bendable manner, in the bending angle plane of the joint part. The tool carrier is coupled to the shank via a roller body pairing for the purpose of ensuring a controlled angulation of the tool carrier relative to the shank and to the joint part. Pull cables which act upon the joint part in a direct manner serve for the control of the angulation of the instrument head.

Hereby, it has found to be disadvantageous that, inherently of the design, only comparatively small moments can be transmitted onto the joint part, for the control of the angulation of the instrument head. A further disadvantage of this instrument lies in the fact that the joint part itself only undergoes a lateral deflection of +/−60° even with a total angular bending of the instrument head of +/−120°, so that the angular bending of the instrument head relative to the shank can only be set in a comparatively coarse manner.

SUMMARY OF THE INVENTION

Against this background, it is the object of the invention, to provide an instrument of the type being discussed, which does not have the disadvantages described above.

The instrument according to the invention is preferably a medical-endoscopic instrument. With regard to this instrument, it can however also be the case of a technoscope which is applied in difficultly accessible cavities of technical objects. As is common with such instruments, the instrument according to the invention also comprises an elongate, preferably straight and rigidly designed shank with an instrument head which is arranged on this shank at the distal side, which is to say distally.

The instrument head comprises at least one joint part which is articulated on the distal shank end in an angularly bendable manner and a tool carrier which at the distal side is articulated on the joint part in an angularly bendable manner in the bending plane of the joint part. According to the invention, a toothing, preferably in the form of a cog segment, is formed at the proximal end of the joint part, wherein this toothing is meshed with a toothed body which is rotatably mounted in the shank and is coupled in movement to a pull cable pair for the control of movement of the instrument head. The angulation of the instrument head is hereby effected by way of a rotational movement of the toothed body, which is caused by tensile loading of one of the pull cables of the pull cable pair, said pull able pair being coupled in movement to the toothed body and acting antagonistically upon the toothed body. With the instrument according to the invention, in contrast to the instruments of the type being discussed here and which have been known until now, it is not necessary to lead the pull cables past the angular bending region between the shank and the instrument head, due to the measure of pivoting the joint part and thus the tool carrier or the complete instrument head via the toothed body arranged in the shank proximally of the articulation of the joint part. Instead, the pull cables are always led to the greatest possible extent in a linear manner in the shank, independently of the angular bending of the instrument head, so that one of the pull cables is moved in the distal direction to the same extent as the other is moved in the proximal direction, with the angular bending of the instrument head.

Preferably, at least one actuator roller which is rotatably mounted in the shank in a manner having the same axis as the toothed body and which is connected to the toothed body in a rotationally fixed manner is provided for the movement coupling of the pull cable pair to the toothed body. The pull cable pair is usefully connected to this actuation roller in a manner such that the actuation roller and the toothed body are rotated in a first direction given a tensile loading of a first pull cable of the pull cable pair, and are rotated in a second, opposite direction given a tensile loading of the other pull cable of the pull cable pair. The fastening of the pull cables of the pull cable pair on the fastening roller is favorably effected peripherally of the fastening roller, wherein the pull cables are fastened on the actuation roller typically on two sides which are opposite to one another with respect to the rotation axis of the actuation roller. Although a component with a circular cross-sectional contour is provided as an actuation roller, however the term "actuation roller" in the context of the invention is also to be basically understood as all components which merely have a part-circular-shaped or part-circular-like peripheral section, around which both pull cables are partly wrapped, but can otherwise have any peripheral contour.

One usefully envisages the actuation roller having an as large as possible effective radius, in order to be able to produce the movement moment necessary for angulation the instrument head, with an as low as possible force effort. The actuation roller arranged in the shank, for this purpose, advantageously has a diameter which corresponds essentially to the inner diameter of the shank. This dimensioning of the actuation roller typically necessitates the actuation roller being rotatably mounted at least in the direct proximity of the middle axis of the shank.

The toothed body is preferably designed in a manner in which it is divided in two, preferably transversely to its rotation axis, wherein the two parts of the toothed body are rotatable relative to one another. In combination with this design, one further advantageously envisages each of the two parts of the toothed body being connected in a rotationally fixed manner to an actuation roller, on which actuation roller in each case a pull cable engages antagonistically with respect to the other pull cable. These design measures serve for preventing a play of the toothing which as the case may be occurs in the case of a single-part toothed body on reversal of the rotation direction of the toothed body, since at least always one of the parts of the toothed body is engaged in a play-free manner with the toothing formed at the proximal end of the joint part, due to the tensioning of the pull cables connected to the two actuation rollers.

The tool carrier is preferably connected to the shank via at least one roller body pairing, in order to ensure a controlled angular bending of the tool carrier relative to the joint part. Thus, one preferably envisages at least one roller body rigidly connected to the shank and being frictionally or preferably positively connected to a roller body rigidly arranged on the tool carrier, being arranged at the distal end of the shank. This, in the case of an angular bending of the joint part which is initiated via the toothed body, leads to a defined rolling movement of the tool-carrier-side roller body on the shank-side roller body, and, entailed by this, leads to a defined angular bending of the instrument head relative to the shank.

The roller bodies of the roller body pairing are preferably designed in a toothed manner. Thus, at least one cog segment which is rigidly connected to the shank and which is meshed with a cog segment rigidly connected to the tool carrier is thus advantageously provided. The type of the toothing which is formed on the cog segments as well as the type of the toothings which are formed on the joint part and the toothed body is basically infinite. The toothings for example can be designed as involute toothing. Such a toothing has the advantage that it reacts comparably insensitively to distance changes of the two cog segments to one another and it requires comparatively little effort for its manufacture. However, the rolling movement of the cog segments with an involute toothing is not effected in a completely slip-free manner, so that undesirable stick-slip effects can arise. Although it is generally possible to counteract these stick-slip effects with grease lubrication or oil lubrication of the toothing, such a measure however is only possible to a limited extent or even not at all in the case of a medical instrument. For this reason, if with regard to the instrument according to the invention, it is the case of a medical endoscopic instrument, it is more useful to apply a toothing which is optimized for a purely rolling friction, such as a cycloidal toothing for example.

The gear ratio (transmission) between the toothed body and the toothed region of the joint part, and the gear ratio of the roller body pairing between the tool carrier and the shank are usefully selected such that an as large as possible moment is available for angularly bending the instrument head.

The toothed body and the toothing of the joint part which is meshed with this toothed body preferably form a step-down gear, which is to say the toothed body has a lower rolling diameter than the toothed region formed on the joint part, so that the angle, about which the joint part is then pivoted on rotating the toothed body, is smaller than the rotation angle of the toothed body. This is advantageous inasmuch as the angle, at which the instrument head can be angularly bent to relative to the shank, can be set particularly precisely in this manner.

Alternatively or additionally to a step-down gear which is formed by the toothed body and the toothing of the joint part, a roller body arranged on the shank side, and a roller body arranged on the tool carrier side, of the roller body pairing, can form a step-down gear between the tool carrier and the shank. Hereby, one envisages the shank-side roller body having a smaller rolling diameter than the tool-carrier-side roller body. With this measure too, one succeeds in the angle, at which the instrument is to be angled relative to the shank, being able to be set in a particularly precise manner.

The step-down gear which is formed by the toothed body and the toothing of the joint part, and the step-down gear which is formed by the two roller bodies of the roller body pairing, between the tool carrier and the shank, are preferably designed such that the moment about the instantaneous center of rotation of the movement is increased with respect to the moment exerted upon the actuation roller, on angularly bending the instrument head. Further preferably, the step-down gear which is formed by the toothed body and the toothing of the joint part, and the step down gear which is formed by the two roller bodies of the roller body pairing, between the tool carrier and the shank, are designed such that the actuation roller and, entailed by this, the toothed body need to be rotated by almost +/−180°, in order to effect an angled bending of the tooth carrier relative to the shank of +/−120°. For this purpose, one preferably envisages the pull cables of the pull cable pair in each case wrapping the actuation roller in an angular range of at least 180°, in a basic position of the instrument, in which the instrument head is arranged in the straight extension of the shank. If an angular bending of the tool carrier different to the previously described one of +/−120° is demanded, then the total step-down of the described roller body pairings with regard to design can be designed such that the maximally possible cable movement results in the demanded angular bending of the tool carrier.

The invention is hereinafter explained in more detail by way of embodiment examples represented in the drawing. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
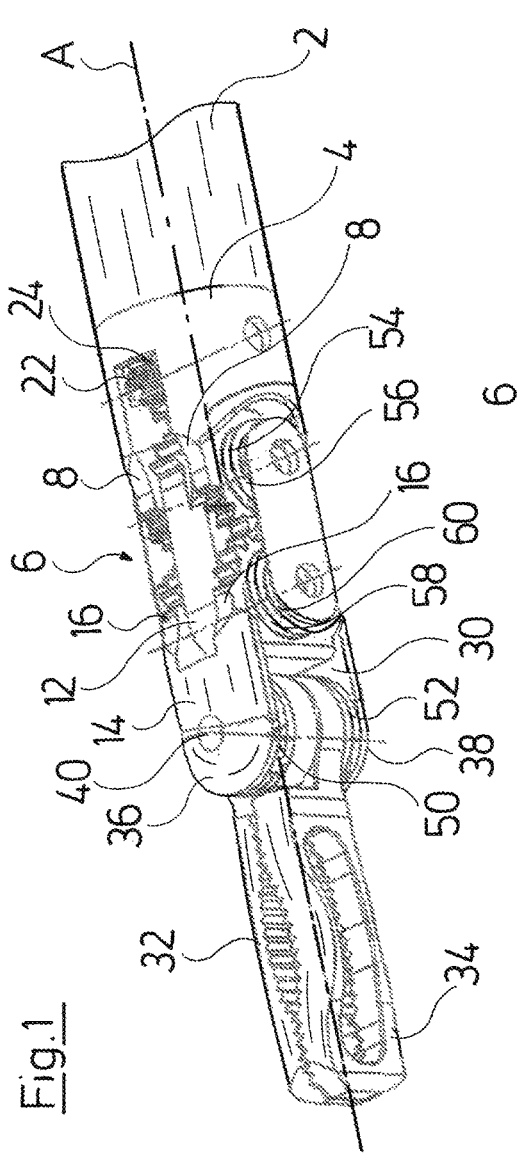
FIG. 1 is a perspective representation showing the distal end of an instrument.

With regard to the instrument represented in the drawing, it is the case of a medical-endoscopic instrument in the form of a forceps. This instrument comprises an elongate shank 2 which is designed in a hollow-cylindrical manner, wherein only the distal end of the shank 2 is represented in the drawing for the purpose of a better overview. The control devices or drives at the proximal end of the shank 2 are not represented, since these can be designed in the known manner.

The distal end of the shank 2 is formed by an end-piece 4. An instrument head 6 connects distally to the end-piece 4. The end-piece 4 designed in a sleeve-like manner, at its distal end comprises two projections 8 which are arranged lying diametrically opposite one another and which project in the longitudinal extension of the shank 2. An elongate joint part 12 is articulated between the two projections 8 via a joint pin 10 which is led through the projections 8. The joint part 12 is part of the instrument head 6.

A tool carrier 14 of the instrument head 6 connects distally to the joint part 12. Two projections 16 which are arranged lying diametrically opposite one another and which extend in the proximal direction are formed on the proximal end of the tool carrier 14, in a manner corresponding to the two projections 8 formed on the end-piece 4. The joint part 12, in the region of the projections 16, is connected in a pivotally movably manner to the tool carrier 14 via a joint pin 18 led through the projections 16, wherein the joint part 12 engages into an intermediate space between the projections 16.

The tool carrier 14 is pivotable relative to the shank, departing from a position, in which the instrument head 6 is aligned in the direct longitudinal extension of the shank 2, and a middle axis A of the shank 2 with a middle axis B of the joint part 12 and a middle axis C of the tool carrier 14 lie in a common plane (FIG. 3), about an angle which is composed of a pivot angle of the joint part 12 relative to the middle axis A of the shank 2 and of a pivot angle of the tool carrier 14 relative to the middle axis B of the joint part 12, on account of the pivotally movable arrangement of the joint part 12 on the projections 8 of the end piece 4 and the pivotally movable arrangement of the tool carrier 14 on the joint part 12. The complete pivot angle hereby lies in an angular range of +/−120°.

Figure 2:
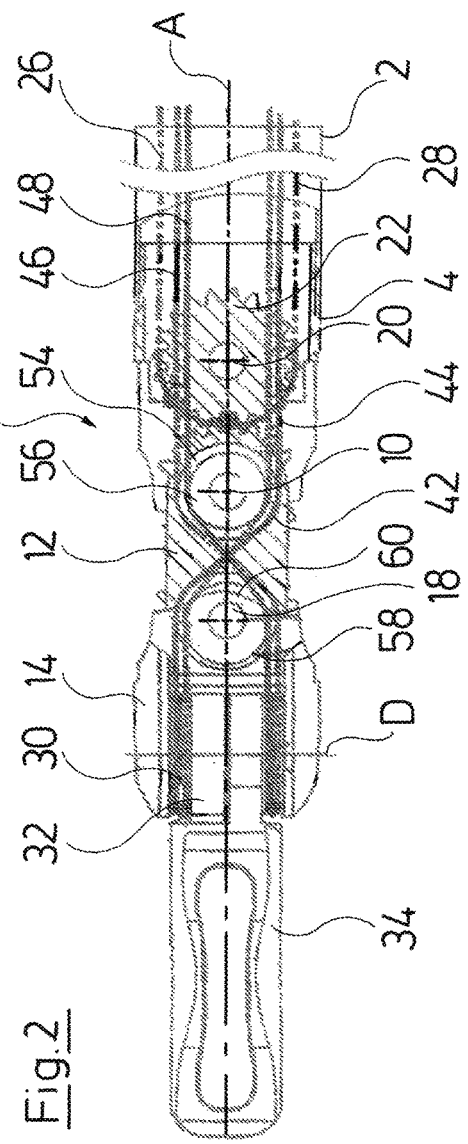
FIG. 2 is a longitudinal sectional view showing the instrument according to FIG. 1.

The end-piece 4 and the tool carrier 14 are connected to one another via a roller body pairing, in order to permit a defined angular bending of the tool carrier 14 relative to the shank 2. The distal ends of the projections 8 formed on the end-piece 4, and the proximal ends of the projections 16 formed on the tool carrier 14 in each case comprise a toothed section in the form of a cog segment, for forming this roller body pairing, wherein the toothed sections which are formed on the projections 8 and 16 mesh with one another. The toothings of the toothed sections of the projections 8 and 16 are designed as a cycloidal toothing. With the embodiment example represented in FIGS. 1 and 2, the toothed sections which are formed on the projections 8 and 16 have the same rolling circle diameter, whereas in the representation according to FIGS. 3 and 4, the rolling circle diameter of the toothed sections formed on the projections 8 are only half as large as that of the toothed sections which are formed on the projections 16, so that the toothed sections which are formed on the projections 8 and 16 form a step-down gear.

A cog-segment-shaped toothing which is meshed with a toothed body 22 which is rotatably mounted on a joint pin 20 in the end piece 4 at the proximal side of the joint part 12 is formed on the rounded proximal end of the joint part 12. The toothing formed on the toothed body 22 as well as the toothing formed on the proximal end of the joint part 12 is designed as a cycloidal toothing. With the embodiment example represented in FIGS. 1 and 2, the rolling circle diameter of the toothing formed on the joint part 12 and the rolling circular diameter of the toothed body 22 are identical, whereas in the representation according to FIGS. 3 and 4, the rolling circle diameter of the toothed body 22 is only half as large as that of the toothing formed on the joint part 12, so that the toothed body 22 with the toothing formed on the joint part 12 forms a step-down gear.

Figure 3:
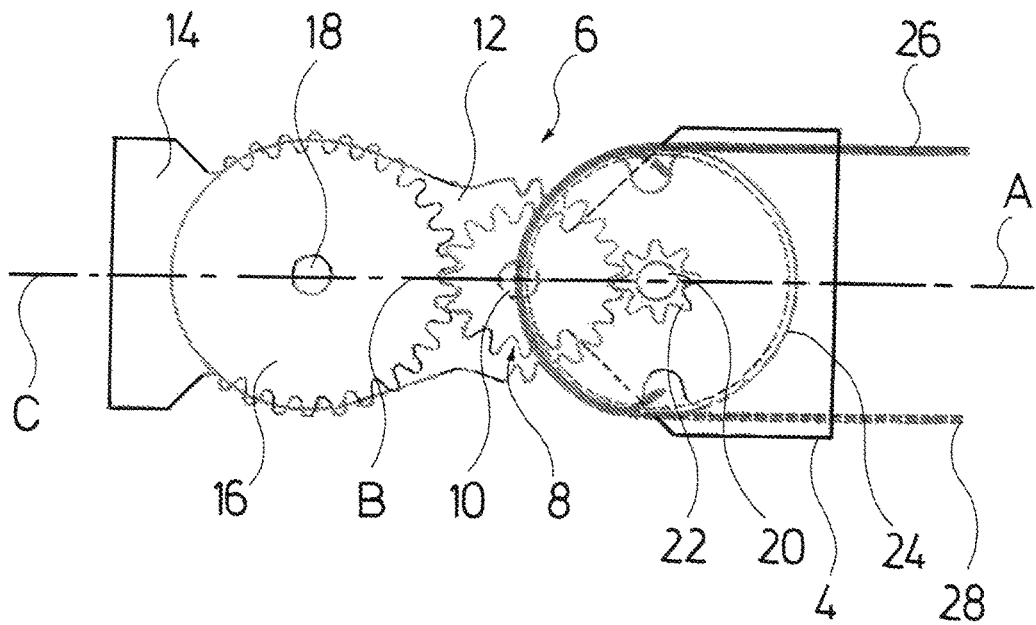
FIG. 3 is a simplified basic representation of the angled bending mechanics between the shank and the tool carrier as well as between the toothed body and the joint part, when the instrument head is not angled.

An actuation roller 24 which is connected to the toothed body 22 in a rotationally fixed manner is also rotatably mounted on the joint pin 20. This actuation roller 24 has an outer diameter which corresponds essentially to the inner diameter of the shank 2. A pull cable pair with pull cables 26 and 28 (FIGS. 3 and 4) is fastened in the actuation roller 24. The fastening of the two pull cables 26 and 28 on the actuation roller 24 is such that the pull cables 26 and 28, in the basic position of the instrument, in which the instrument head 6 is arranged in the straight extension of the shank 2, in each case wrap the actuation roller 24 in an angular range of 180° (FIG. 3). The pull cables 26 and 28, departing from the actuation roller 24, are led to the proximal end of the shank 2. There, at the proximal side of the shank 2, the pull cables 26 and 28 are connected to a control device which is not represented in the drawing, with which control device it is the case of a handle which is to be manually actuated or of a control interface of a robotic operation system, depending on the type of instrument. The angled bending of the instrument head 6 is controlled by the control device.

The tool carrier 14 at the distal side comprises an indentation 30 which is open to the distal end of the tool carrier 14. Two jaw parts 32 and 34 of a jaw tool are articulated in the indentation 30. The articulation of the jaw parts 32 and 34 in the indentation 30 is effected via a joint pin which is not represented in the drawing and which is led through holes 40 formed on two wall sections 36 and 38 delimiting the indentation 30. The joint pin forms a pivot axis D, about which the jaw parts 32 and 34 are pivotable in a plane normally to the angulation plane of the instrument head 6.

Pull cables 42, 44, 46 and 48 (FIG. 2) serve for the control of the jaw parts 32 and 34. The pull cables 42 and 44, at the distal side, are fastened on an actuation roller 50 which is connected to the jaw part 32 in a rotationally fixed manner and which is rotatable about the pivot axis D of the jaw parts 32 and 34. In a manner corresponding to this, the pull cables 46 and 48 are fastened on an actuation roller 52 which is rotatable about the pivot axis D and which is connected to the jaw part 34 in a rotationally fixed manner.

In each case a guide roller 54 is rotatably mounted on the joint pin 10, at the outer side of the projections 8 which are formed on the end piece 4. Furthermore, a further guide roller 56 is mounted in each case on the joint pin 10, at the outer side of the guide roller 54. On the joint pin 18 too, a guide roller 58 is also rotatably mounted in each case at the outer side of the projections 16 formed on the tool carrier 14, and a guide roller 60 rotatably mounted in each case at the outer side of the guide rollers 58. The guide rollers 54, 56, 58 and 60 which are visible in FIG. 1 are once again located in the rear region of the instrument head 6 which is not visible, in an arrangement which is mirrored at the middle axis B. The guide rollers 54 and 58 in the region of the angular bending of the instrument head 6 serve for guiding the pull cables 42 and (not visible in the rear region) 46 which are led through the shank 2 to the proximal side of the shank 2, whereas the guide rollers 56 and 60 serve for guiding the pull cables (not visible in the rear region) 44 and 48 which are led through the shank 2 to the proximal side of the shank 2. The leading or guiding of the pull cable 42 through the instrument head 6 is effected by the guide rollers 54 and 58. The leading of the pull cable 48 is effected by the guide rollers 56 and 60. Thereby, the pull cables 42 and 48 cross in an intermediate space between the guide rollers 54, 56, 58 and 60 without contacting. In the same manner, the pull cables 44 and 46 cross in the rear, non-visible region between the guide rollers, without contacting. The pull cables 42, 44, 46 and 48 at the proximal side of the shank 2 are coupled in movement to a control device, for the control of the jaw parts 32 and 34, with which control device it can be the case of a handle or a control interface of a robotic operation system, depending on whether the instrument is an instrument to be manually operated or is part of a robotic operation system.

Figure 4:
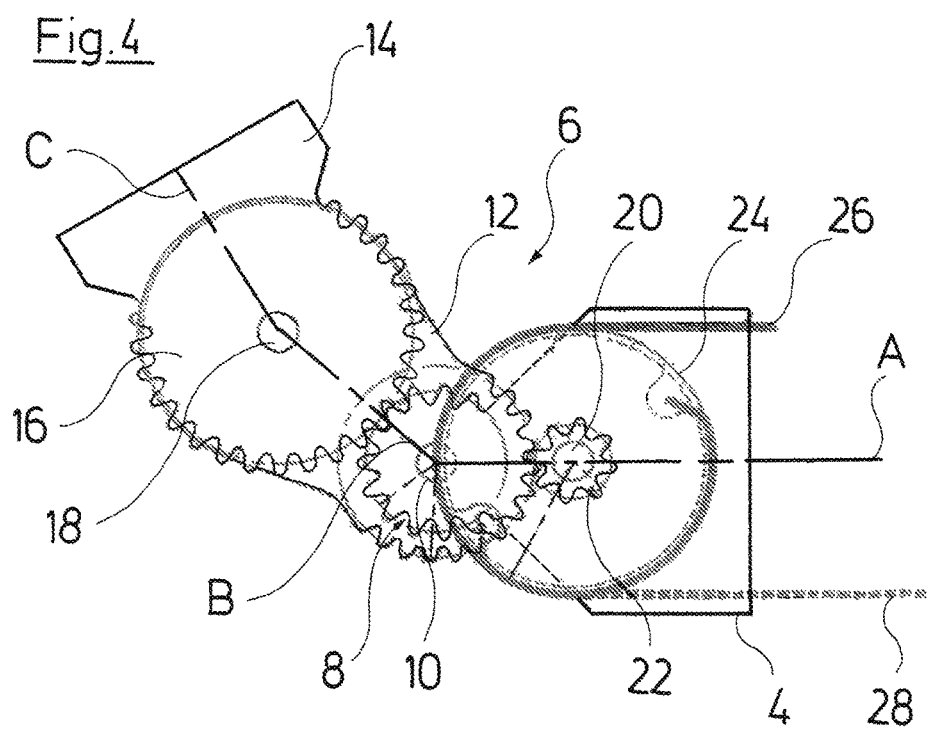
FIG. 4 is a simplified basic representation of the angular bending mechanics between the shank and the tool carrier as well as between the toothed body and the joint part, in the case of an angularly bent instrument head.

The control of the angular bending of the instrument head 6 is hereinafter explained in more detail by way of FIGS. 3 and 4. The pull cable 28 is loaded in tension, starting from the position which is represented in FIG. 3 and in which the instrument head 6 is aligned in the direct longitudinal extension of the shank 2. The actuation roller 24 and the toothed body 22 which is connected to this in a rotational fixed manner is rotated in the anti-clockwise direction by way of this, which in turn results in a pivot movement of the joint part 12 in the clockwise direction (FIG. 4). During the pivot movement of the joint parts 12, the toothings of the toothed sections formed on the projections 16 of the tool carrier 14 roll on the toothed sections formed on the projections 16 on the end part 4, so that a pivot movement of the tool carrier 14 is superimposed on the pivot movement of the joint part 12. Hereby, the selected gear ratios with the roller body pairings of the projections 8 with the projections 16, and with the roller body pairing of the toothed body 22 with the joint part 12 have the effect that the moment about the instantaneous center of rotation of the movement is increased compared to the movement exerted upon the actuation roller 24, and the actuation roller 24 must be rotated by almost 180°, so as to result in a total bending of the instrument head 6 of 120°.

Figure 5:
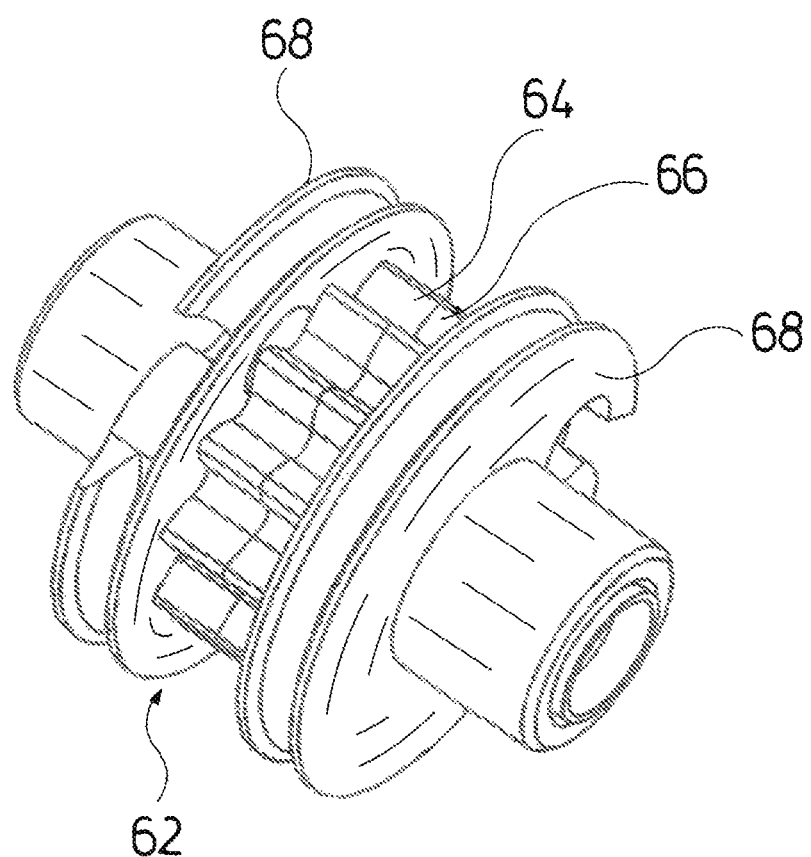
FIG. 5 is a perspective representation of a toothed body which is designed in a manner divided into two.

An alternative to the toothed body 62 which can be applied alternatively to the toothed body 22 represented in FIGS. 1 to 4 is represented in FIG. 5. This toothed body 62 is divided in two transversely to its rotation axis and comprises two parts 64 and 66. The two parts 64 and 66 of the toothed body are rotatable relative to one another. An actuation roller 68 is connected in a rotationally fixed manner to the parts 64 and 66, at the face sides of these parts which are away from one another. A pull cable which is tensioned and which is not represented in the drawing is connected to each of the actuation rollers for actuating the toothed body 62. The fastening of the pull cables on the actuation rollers 68 is such that the pull cables act antagonistically (in opposition) upon the toothed body 62.

While specific embodiments of the invention have been shown and described in detail to illustrate the application of the principles of the invention, it will be understood that the invention may be embodied otherwise without departing from such principles.

The invention claimed is:

1. An instrument comprises a medical endoscopic instrument or technoscope, the instrument further comprising:
a shank;
a toothed body rotatably mounted in the shank;
a pull cable pair; and
an instrument head, said instrument head comprising:
at least one joint part articulated on a distal shank end, of the shank, in an angularly bendable manner; and
a tool carrier which, at a tool carrier distal side, is articulated on the at least one joint part in an angularly bendable manner in an angular bending plane of the at least one joint part, wherein a toothing, which is meshed with the toothed body rotatably mounted in the shank and coupled in movement to the pull cable pair for the movement control of the instrument head, is formed at a proximal end of the joint part, the toothed body being divided in two, transversely to a rotation axis thereof, wherein two parts of the toothed body are rotatable relative to one another, one of the two parts of the toothed body being connected in a rotationally fixed manner to an actuation roller and another of the two parts of the toothed body being connected in a rotationally fixed manner to another actuation roller, wherein one pull cable of the pull cable pair engages the actuation roller and another pull cable of the pull cable pair engages the another actuation roller.

2. An instrument according to claim 1, wherein the pull cable pair is connected to the actuation roller which is rotatably mounted in the shank in a manner having a same axis as the toothed body, the actuation roller comprising a groove, the groove defining a portion of a guide path of the one pull cable, the another actuation roller comprising another groove, the another groove defining a portion of another guide path of the another pull cable.

3. An instrument according to claim 2, wherein the actuation roller has a diameter which corresponds essentially to an inner diameter of the shank.

4. An instrument according to claim 1, wherein the toothed body and a toothed section which is formed at the proximal end of the joint part comprise a cycloidal toothing, the actuation roller is located at a spaced location from the another actuation roller.

5. An instrument according to claim 1, wherein the tool carrier is coupled in movement to the shank via at least one roller body pairing.

6. An instrument according to claim 5, wherein the at least one roller body pairing comprises roller bodies, wherein the roller bodies of the roller body pairing are configured with teeth.

7. An instrument according to claim 1, wherein the toothed body and the toothing of the joint part which is meshed with the toothed body form a step-down gear, the one of the two parts of the toothed body comprising a plurality of first teeth, the another of the two parts of the toothed body comprising a plurality of second teeth, the first teeth being located opposite the second teeth in a direction parallel to the rotation axis.

8. An instrument according to claim 5, wherein a roller body which is arranged on the shank side and a roller body arranged on the tool carrier side form a step-down gear.

9. An instrument according to claim 2, wherein the pull cables of the pull cable pair wrap the actuation roller in each case in an angular range of at least 180°, in a basic position of the instrument, in which the instrument head is arranged in the straight extension of the shank.

10. An instrument according to claim 2, wherein the actuation roller is located directly adjacent to the toothed body, wherein the actuation roller and the toothed body rotate based on actuation of the pull cable pair, wherein the toothed body does not rotate relative to the actuation roller.

11. An instrument according to claim 10, wherein the toothed body is located at a spaced location from the pull cable pair.

12. An instrument according to claim 2, further comprising:
- another pull cable pair;
- a plurality of guide rollers, one of the guide rollers being located on one side of the toothed body and another one of the guide rollers being located on one side of the joint part teeth, the another pull cable pair being connected to the plurality of guide rollers, the tool carrier being connected to a tool, the tool being actuated based on actuation of the another pull cable pair.

13. An instrument according to claim 1, wherein the toothed body is located between the one actuation roller and the another actuation roller.

14. An instrument according to claim 1, wherein the toothed body comprises a first toothed body portion and a second toothed body portion, the first toothed body portion comprising a first toothed body portion surface, the second toothed body portion comprising a second toothed body portion surface, the first toothed body portion surface being located opposite the second toothed body portion surface in a direction parallel to the rotation axis.

15. An instrument according to claim 1, wherein the actuation roller guides at least a portion of the one pull cable about the one of the two parts of the toothed body, the another actuation roller guiding at least another portion of the another pull cable about the another one of the two parts of the toothed body.

16. An instrument comprises a medical endoscopic instrument or technoscope, the instrument further comprising:
- a shank comprising a distal shank end portion;
- a toothed body rotatably mounted to the shank such that the toothed body is rotatable relative to the shank, the toothed body being divided in two parts, transversely to a rotation axis thereof, the two parts of the toothed body being rotatable relative to one another and rotatable relative to the shank;
- a pull cable pair;
- an instrument head, the instrument head comprising at least one joint part and a tool carrier, the at least one joint part comprising a proximal end portion, the proximal end portion comprising joint part teeth, the tool carrier comprising a tool carrier distal side, the at least one joint part being articulated on the distal shank end portion such that the at least one joint part is angularly bendable relative to the distal shank end portion, the tool carrier, at the tool carrier distal side, being articulated on the at least one joint part in an angularly bendable manner in an angular bending plane of the at least one joint part, the joint part teeth engaging the toothed body, wherein the joint part and the tool carrier are actuated based on movement of the pull cable;
- a first cable;
- a second cable;
- a first actuation roller, wherein the first cable is connected to the first actuation roller, the first actuation roller being rotatably mounted in the shank and the first actuation roller is connected to the one of the two parts of the toothed body in a rotationally fixed manner;
- a second actuation roller, wherein the second cable is connected to the second actuation roller, the second actuation roller being rotatably mounted in the shank and the second actuation roller being connected to the another one of the two parts of the toothed body in a rotationally fixed manner, the first actuation roller being located on one side the toothed body and the second actuation roller being located on another side of the toothed body.

17. An instrument according to claim 16, wherein each of the first actuation roller and the second actuation roller has a diameter which corresponds essentially to an inner diameter of the shank.

18. An instrument according to claim 16, wherein the toothed body is located at a spaced location from the pull cable pair.

19. An instrument according to claim 16, further comprising:
- another pull cable pair;
- a plurality of guide rollers, one of the guide rollers being located on one side of the toothed body and another one of the guide rollers being located on one side of the joint part teeth, the another pull cable pair being connected to the plurality of guide rollers, the tool carrier being connected to a tool, the tool being actuated based on actuation of the another pull cable pair.

20. An instrument comprising a medical endoscopic instrument or technoscope, the instrument further comprising:
- a shank comprising a distal shank end portion;
- a toothed body rotatably mounted to the shank such that the toothed body is rotatable relative to the shank, the toothed body being divided in two parts, transversely to a rotation axis thereof, the two parts of the toothed body being rotatable relative to one another and rotatable relative to the shank;
- a pull cable pair;
- an instrument head, the instrument head comprising at least one joint part and a tool carrier, the at least one joint part comprising a proximal end portion, the proximal end portion comprising joint part teeth, the tool carrier comprising a tool carrier distal side, the at least one joint part being articulated on the distal shank end portion such that the at least one joint part is angularly bendable relative to the distal shank end portion, the tool carrier, at the tool carrier distal side, being articulated on the at least one joint part in an angularly bendable manner in an angular bending plane of the at least one joint part, the joint part teeth engaging the toothed body, wherein the joint part and the tool carrier are actuated based on movement of the pull cable;
- a first cable;
- a second cable;
- a first actuation roller, wherein the first cable is connected to the first actuation roller, the first actuation roller being rotatably mounted in the shank and the first actuation roller is connected to the one of the two parts of the toothed body in a rotationally fixed manner;
- a second actuation roller, wherein the second cable is connected to the second actuation roller, the second actuation roller being rotatably mounted in the shank and the second actuation roller being connected to the another one of the two parts of the toothed body in a rotationally fixed manner, wherein the two parts of the toothed body are located between the first actuation roller and the second actuation roller.

* * * * *